United States Patent
Yoshida et al.

(10) Patent No.: US 8,689,637 B2
(45) Date of Patent: Apr. 8, 2014

(54) FRACTURE ANALYSIS METHOD, DEVICE, AND PROGRAM FOR SPOT WELDED PORTION, AND COMPUTER-READABLE RECORDING MEDIUM

(75) Inventors: Hiroshi Yoshida, Tokyo (JP); Naruhiko Nomura, Tokyo (JP); Akihiro Uenishi, Tokyo (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 0 days.

(21) Appl. No.: 13/634,365

(22) PCT Filed: Apr. 6, 2011

(86) PCT No.: PCT/JP2011/058738
§ 371 (c)(1),
(2), (4) Date: Sep. 12, 2012

(87) PCT Pub. No.: WO2011/126057
PCT Pub. Date: Oct. 13, 2011

(65) Prior Publication Data
US 2013/0000415 A1 Jan. 3, 2013

(30) Foreign Application Priority Data
Apr. 7, 2010 (JP) ................................ 2010-088271

(51) Int. Cl.
*G01N 3/08* (2006.01)
*G01N 3/24* (2006.01)

(52) U.S. Cl.
USPC .................... 73/827; 73/821; 73/842; 73/845

(58) Field of Classification Search
None
See application file for complete search history.

(56) References Cited

U.S. PATENT DOCUMENTS

| 4,299,120 | A | * | 11/1981 | Barker ............................... 73/87 |
| 7,672,819 | B2 | | 3/2010 | Kumagai |
| 8,027,819 | B2 | | 9/2011 | Yoshida et al. |

(Continued)

FOREIGN PATENT DOCUMENTS

| JP | 2005-148053 | 6/2005 |
| JP | 2005-315854 | 11/2005 |

(Continued)

OTHER PUBLICATIONS

International Search Report dated Jun. 28, 2011, issued in corresponding PCT Application No. PCT/JP2011/058738.

(Continued)

*Primary Examiner* — Andre Allen
(74) *Attorney, Agent, or Firm* — Kenyon & Kenyon LLP

(57) ABSTRACT

Maximum allowable load values of a welded portion in respective fracture modes of a load fracture, a moment fracture, and a nugget interior fracture are found based on at least one of a sheet thickness t, a tensile strength TS, an elongation El, and a chemical composition of a nugget portion in each of spot-welded steel sheets, a nugget diameter d of a welded portion, an effective width B of the welded portion determined by a distance between adjacent welded portions, edges or ridge lines, and a sectional height H. Then, according to these fracture modes, an allowable load value at every moment after the maximum allowable load value of the welded portion is reached is found, and a displacement or a time at which the allowable load value becomes 0, that is, at which a complete fracture occurs is found, thereby finding a fracture limit.

8 Claims, 7 Drawing Sheets

(56) References Cited

U.S. PATENT DOCUMENTS

2007/0090165 A1* 4/2007 Kumagai ............... 228/101
2007/0102480 A1* 5/2007 Lip ....................... 228/101
2007/0199924 A1* 8/2007 Yoshida et al. ......... 219/109

FOREIGN PATENT DOCUMENTS

| JP | 2005-326401 | 11/2005 |
| JP | 2007-024788 | 2/2007 |
| JP | 2007-114046 | 5/2007 |
| JP | 2007-263830 | 10/2007 |
| JP | 2007-304005 | 11/2007 |
| JP | 2008-107322 | 5/2008 |
| JP | 2008-157882 | 7/2008 |
| JP | 2009-265028 | 11/2009 |

OTHER PUBLICATIONS

International Preliminary Report on Patentability dated Nov. 15, 2012, issued in corresponding PCT Application No. PCT/JP2011/058738.

Diego J. Celentano et al., "Characterization of the mechanical behaviour of materials in the tensile test: experiments and simulation", Modelling and Simulation in Materials Science and Engineering, IOP Publishing, Bristol, GB, vol. 12, No. 4, pp. S425-S444, Jul. 1, 2004.

Extended European Search Report dated Nov. 6, 2013 issued in corresponding EP Application No. 11765957.3.

* cited by examiner

F I G. 5A
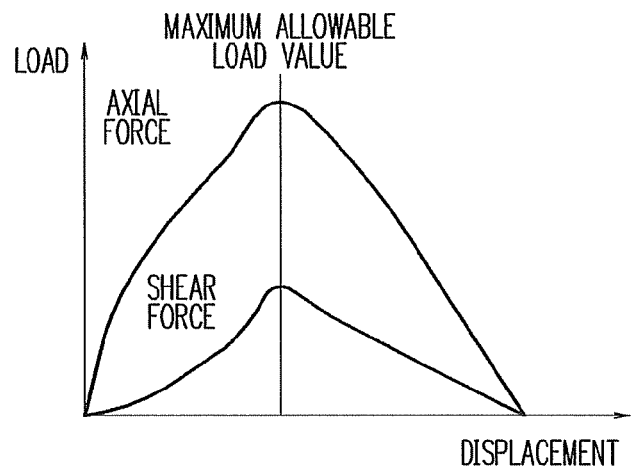
F I G. 5B
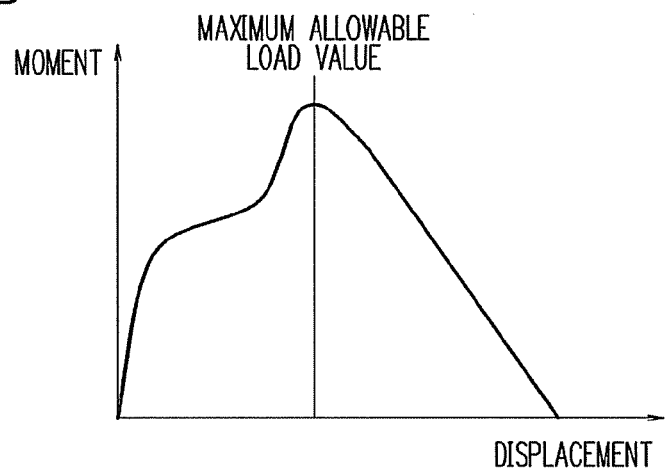
F I G. 5C
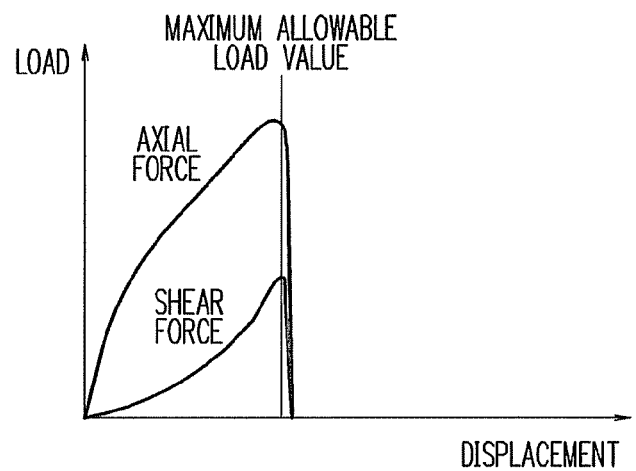

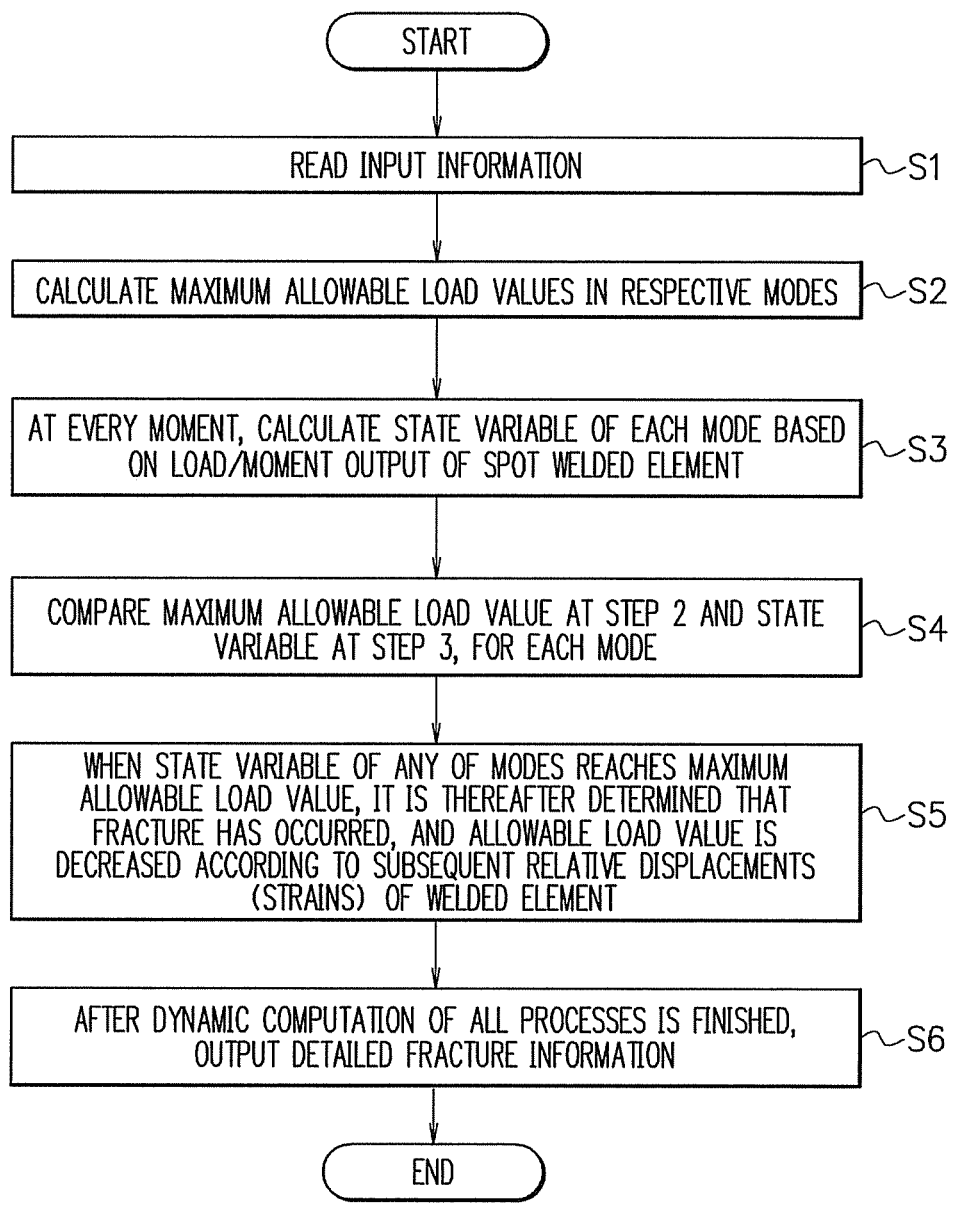

F I G. 7
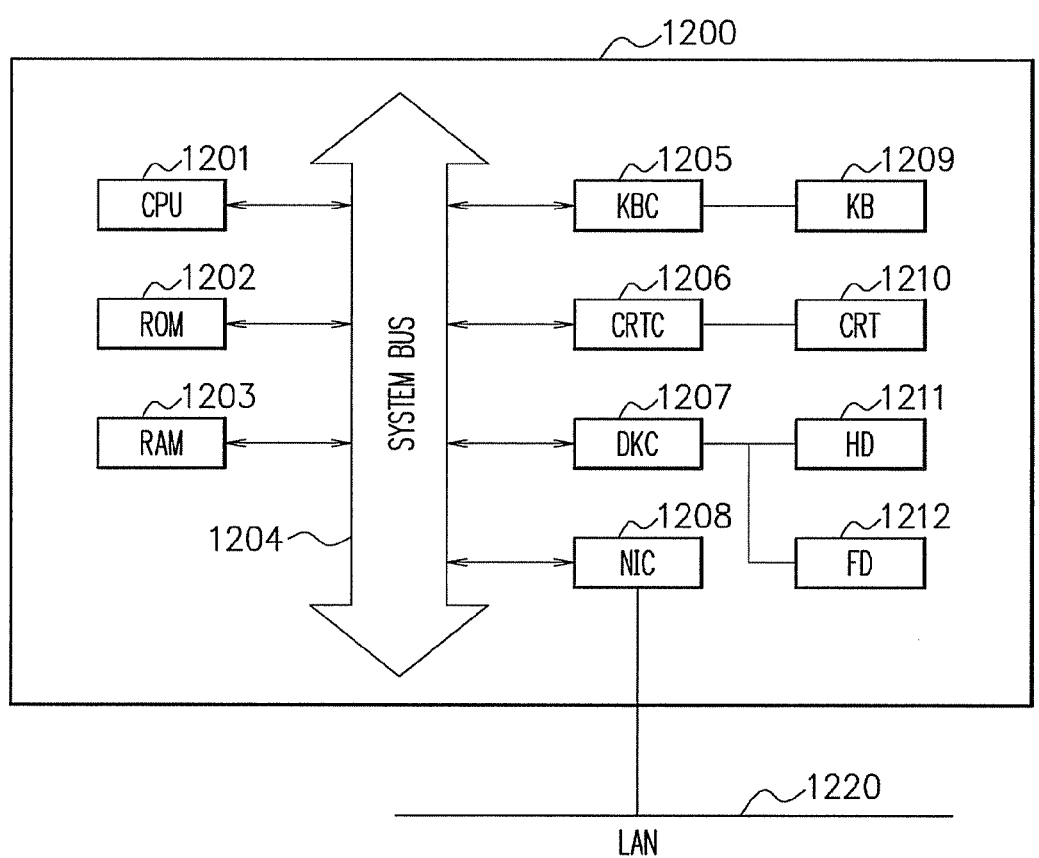

F I G. 8
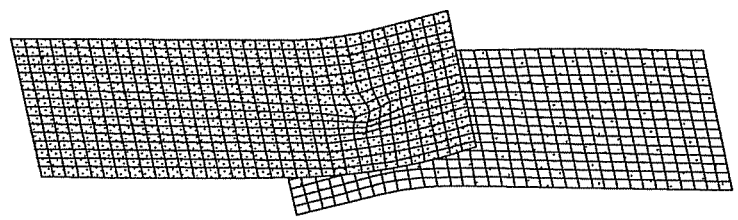

F I G. 9A     F I G. 9B
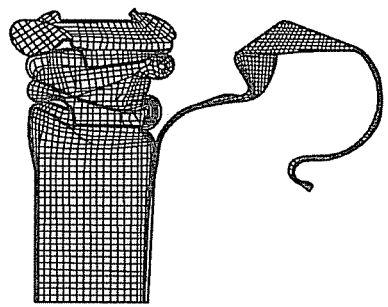 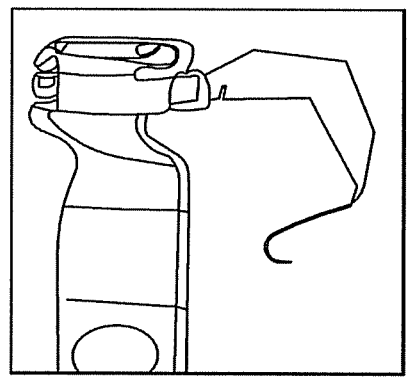
F I G. 10
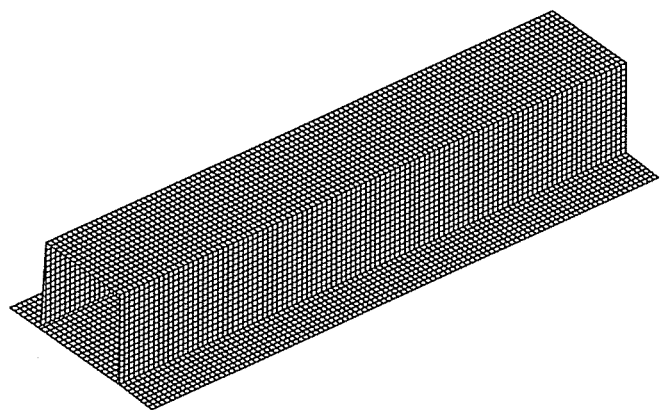

FRACTURE ANALYSIS METHOD, DEVICE, AND PROGRAM FOR SPOT WELDED PORTION, AND COMPUTER-READABLE RECORDING MEDIUM

This application is a national stage application of International Application No. PCT/JP2011/058738, filed Apr. 6, 2011, which claims priority to Japanese Application No. 2010-088271, filed Apr. 7, 2010, the content of which is incorporated by reference herein in its entirety.

TECHNICAL FIELD

The present invention relates to a method, a device, and a program for analyzing a fracture of a spot welded portion in a car crash simulation and the like, and a computer-readable storage medium.

BACKGROUND ART

In an automotive industry, it has recently become an urgent need to develop a car body structure capable of reducing an injury to a passenger at the time of a crash. It is possible to realize such a car body structure excellent in crash safety by absorbing impact energy at the time of the crash by structural members except a passenger section to minimize deformation of the passenger section, thereby securing survival space. That is, it is important that the structural members absorb the impact energy.

A main structural member absorbing the impact energy at a full-lap collision or an offset collision of an automobile is a front side member. A cross section of the front side member is closed by spot welding after stamping or the like. Generally, a buckling occurs in this front side member so as to absorb the impact energy. In order to improve the absorption of the impact energy, it is important to stabilize a buckling mode so as not to cause a bending or a fracture halfway.

The spot welding of the member has a problem that, unless a spot welding interval, a nugget diameter, and a welding condition are optimized to stabilize the buckling, a fracture occurs from a welded point during the buckling to cause an unstable buckling mode, resulting in reduction in the absorption of the impact energy.

In order to solve this type of problem, conditions realizing stable buckling without causing any fracture at a welded point have been conventionally studied by experimentally manufactured member under varied spot welding intervals and conducting a buckling test.

This method, however, requires trials and errors, that is, the experimental manufacture and the test are necessary for each automobile and each member. This has problems that the manufacture is costly and it takes a long time for designing.

As a method of estimating a fracture limit of a spot welded portion, various proposals have been conventionally made, and for example, Japanese Laid-open Patent Publication No. 2005-148053 (the undermentioned Patent Literature 1) describes a method in which a shear tensile test or a cross tensile test of a test piece having a spot welded portion is conducted to find, in advance, a relation of a ratio of a nugget diameter d to a width of the test piece and a stress concentration factor α, and fracture limit loads of the shear tensile test and the cross tensile test are estimated for a material having a given tensile strength, whereby a fracture limit load in a new test condition or in a spot welded portion of an actual member is estimated.

Further, Japanese Laid-open Patent Publication No. 2005-315854 (the undermentioned Patent Literature 2) describes a method in which a tensile test of a flange having a spot welded portion is conducted, moment efficiency γ is found in advance from a bending moment applied to an end portion of the spot welded portion and a full plastic moment Mp theoretically calculated from a sheet thickness, a sheet width, and a strength characteristic of a sample sheet, and from this moment efficiency γ and a full plastic moment Mp' to a material having a given sheet thickness, sheet width, and strength characteristic, a fracture limit moment of a spot welded portion in the flange tensile test is estimated.

Further, Japanese Laid-open Patent Publication No. 2005-326401 (the undermentioned Patent Literature 3) describes a method in which based on a cross tensile test and/or a shear tensile test of a spot welded joint, a fracture strength parameter of a spot welded portion in cross tension and/or shear tension is calculated from all or one of a material strength, a sheet thickness, a spot-welding nugget diameter, a sheet width of the joint, and a rotation angle of the joint in the tensile test, the fracture strength parameter of each type of steel is stored, and the stored fracture strength parameter is introduced into a fracture prediction formula in which deformation of a periphery of the spot welding is modeled by a finite element method, and a fracture of the spot welded portion is determined.

Further, Japanese Laid-open Patent Publication No. 2007-304005 (the undermentioned Patent Literature 4) describes a method in which, based on a cross tensile test and/or a shear tensile test of a spot-welded joint, some or all of a sheet thickness, a spot-welding nugget diameter, a material strength of a base material, and a fracture elongation, and one or both of a joint welding interval and a joint length perpendicular to the welding interval are input to a computer, the computer calculates, from the input data, a rupture strain parameter of a spot welded portion in cross tension and/or shear tension, the rupture strain parameter of each type of steel is stored in a parameter storage, the rupture strain parameter stored in the parameter storage is introduced into a rupture prediction formula in which deformation of the periphery of the spot welding is modeled by a finite element method, and a rupture of the spot welded portion is determined, whereby a rupture of a spot welded portion of, for example, an automobile member is predicted in finite element method analysis on the computer.

CITATION LIST

Patent Literature

Patent Literature 1: Japanese Laid-open Patent Publication No. 2005-148053
Patent Literature 2: Japanese Laid-open Patent Publication No. 2005-315854
Patent Literature 3: Japanese Laid-open Patent Publication No. 2005-326401
Patent Literature 4: Japanese Laid-open Patent Publication No. 2007-304005

SUMMARY OF INVENTION

Technical Problem

However, in any of the patent literatures, an allowable load value before a complete fracture occurs after a maximum allowable load value of the welded portion is reached is not found. Further, any of these methods cannot cope with a load fracture which is a fracture due to tension acting on a spot welded portion (hereinafter also referred to as a load-type base material-plug fracture), a moment fracture which is a fracture due to a bending moment applied to an end portion of a spot welded portion (hereinafter also referred to as a moment-type base material-plug fracture), and a nugget interior fracture which is a fracture due to a shear force acting on a spot welded portion.

The present invention was made in consideration of the problems of the conventional arts described above and has an object to make it possible to find an allowable load value before a complete fracture occurs after a maximum allowable load value of a welded portion is reached.

Solution to Problem

The present invention was made as a result of studious studies for solving the aforesaid problems and its gist is as follows.

(1) A fracture analysis method for a spot welded portion including:

a procedure to find a maximum allowable load value of a welded portion in a predetermined fracture mode based on at least one of a sheet thickness t, a tensile strength TS, an elongation El, and a chemical composition of a nugget portion in each of spot-welded steel sheets, a nugget diameter d of the welded portion, an effective width B of the welded portion determined by a distance between adjacent welded portions, edges or ridge lines, and a sectional height H; and a procedure to find an allowable load value at every moment after the maximum allowable load value of the welded portion is reached, according to the predetermined fracture mode, to find a displacement or a time at which the allowable load value becomes 0.

(2) The fracture analysis method for the spot welded portion described in (1), wherein as the predetermined mode, a load fracture, a moment fracture, and a nugget interior fracture are used.

(3) The fracture analysis method for the spot welded portion described in (1), wherein the predetermined fracture mode is a moment fracture and the maximum allowable load value thereof is corrected by the sectional height H.

(4) The fracture analysis method for the spot welded portion described in (1), wherein the predetermined fracture mode is a nugget interior fracture, and in finding the maximum allowable load value thereof, a thickness-direction weighted average $C_{eq}$ of a nugget portion carbon equivalent, expressed by the following formula is used as a kind i (i=1 to n) of a welded test piece.

$$C_{eq} = \Sigma_{i=1}^{n}\{t_i \cdot C_{eq}^i\}/\Sigma_{i=1}^{n}\{t_i\}$$

(5) The fracture analysis method for the spot welded portion described in (1), wherein in the procedure to find the maximum allowable load value, when the number of the welded steel sheets is three or more, two welded portions or more where the three steel sheets or more are joined are separately subjected to the determination, and in the determination, as the sheet thickness of the steel sheet stacked on a rear surface side, a total sheet thickness of the steel sheets stacked on the rear surface side is adopted.

(6) The fracture analysis method for the spot welded portion described in (1), wherein detailed fracture information is output.

(7) A fracture analysis device for a spot welded portion including:

a means for finding a maximum allowable load value of a welded portion in a predetermined fracture mode based on at least one of a sheet thickness t, a tensile strength TS, an elongation El, and a chemical composition of a nugget portion in each of spot-welded steel sheets, a nugget diameter d of the welded portion, an effective width B of the welded portion determined by a distance between adjacent welded portions, edges or ridge lines, and a sectional height H; and a means for finding an allowable load value at every moment after the maximum allowable load value of the welded portion is reached, according to the predetermined fracture mode, to find a displacement or a time at which the allowable load value becomes 0.

(8) A program causing a computer to execute:

processing to find a maximum allowable load value of a welded portion in a predetermined fracture mode based on at least one of a sheet thickness t, a tensile strength TS, an elongation El, and a chemical composition of a nugget portion in each of spot-welded steel sheets, a nugget diameter d of the welded portion, an effective width B of the welded portion determined by a distance between adjacent welded portions, edges or ridge lines, and a sectional height H; and processing to find an allowable load value at every moment after the maximum allowable load value of the welded portion is reached, according to the predetermined fracture mode, to find a displacement or a time at which the allowable load value becomes 0.

(9) A computer-readable storage medium storing a program causing a computer to execute:

processing to find a maximum allowable load value of a welded portion in a predetermined fracture mode based on at least one of a sheet thickness t, a tensile strength TS, an elongation El, and a chemical composition of a nugget portion in each of spot-welded steel sheets, a nugget diameter d of the welded portion, an effective width B of the welded portion determined by a distance between adjacent welded portions, edges or ridge lines, and a sectional height H; and processing to find an allowable load value at every moment after the maximum allowable load value of the welded portion is reached, according to the predetermined fracture mode, to find a displacement or a time at which the allowable load value becomes 0.

Advantageous Effects of Invention

According to the present invention, the allowable load value at every moment after the maximum allowable load value of the welded portion is reached is found according to the predetermined fracture mode, and the displacement or the time at which the allowable load value becomes 0 is found, which makes it possible to find the allowable load value before a complete fracture occurs. Further, according to a property and a load state of the spot welded portion, it is possible to estimate a right fracture behavior even when it is not known in advance which fracture mode will occur. Further, the handling when the number of the steel sheets is three or more and the output of the detailed information can facilitate consideration of a technique for fracture prevention measure.

BRIEF DESCRIPTION OF DRAWINGS

FIG. 5A is a chart showing a method of decreasing an allowable load value in a load fracture.

FIG. 5B is a chart showing a method of decreasing an allowable load value in a moment fracture.

FIG. 5C is a chart showing a method of decreasing an allowable load value in a nugget interior fracture.

FIG. 6 is a flowchart showing calculation steps in this embodiment.

FIG. 7 is a block diagram showing an example of a computer system capable of configuring the fracture analysis device for the spot welded portion.

FIG. 8 is a view showing an example of an analysis model used in an example.

FIG. 9A is a view used to explain a state of a fracture of a spot welded portion at the time of a dynamic crushing test of a member in an example and is a view showing an analysis result.

FIG. 9B is a view used to explain a state of a fracture of a spot welded portion at the time of a dynamic crushing test of the member in the example and is a view schematically showing a photograph of a test result by means of a graphic.

FIG. 10 is a view showing an example of an analysis model used in an example.

DESCRIPTION OF EMBODIMENTS

Hereinafter, a suitable embodiment of the present invention will be described with reference to the attached drawings.

Figure 1:
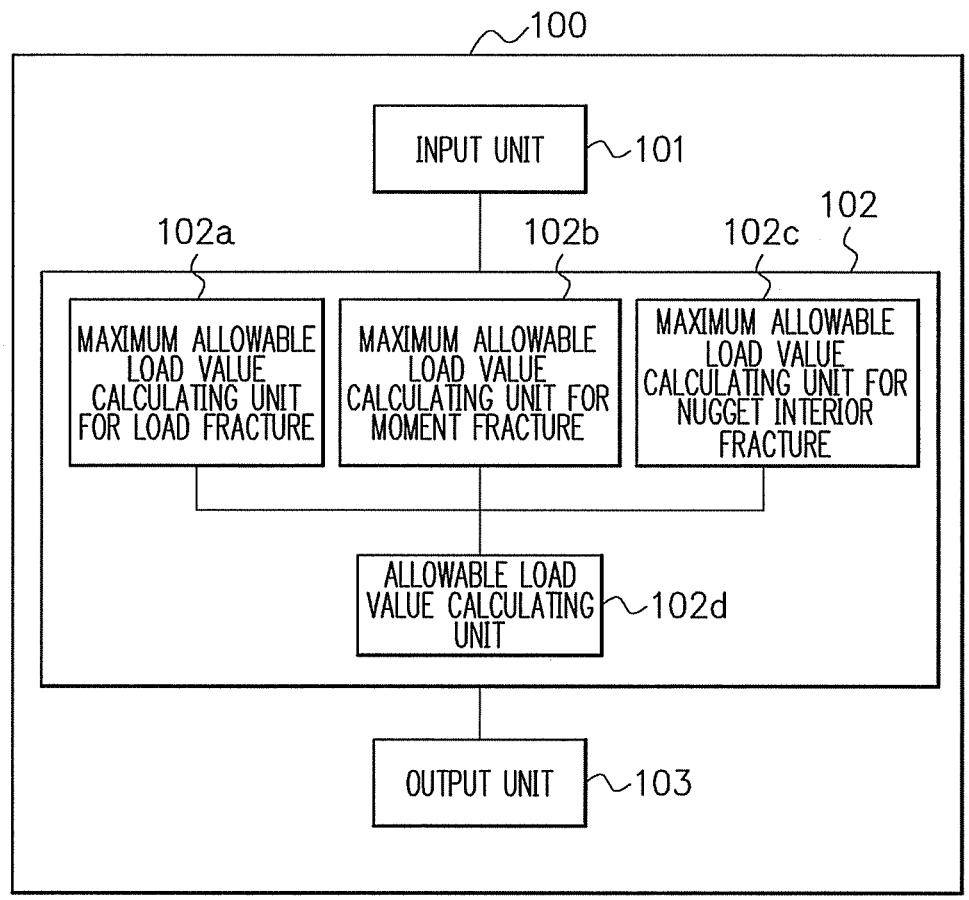
FIG. 1 is a diagram showing a structure of a fracture analysis device for a spot welded portion according to this embodiment.

FIG. 1 is a diagram showing a structure of a fracture analysis device 100 for a spot welded portion according to this embodiment. 101 denotes an input part, to which a sheet thickness t, a tensile strength TS, an elongation El, and a chemical composition of a nugget portion in each of spot-welded steel sheets, a nugget diameter d of a welded portion, an effective width B determined by a distance between adjacent welded portions, edges or ridge lines, and a sectional height H are input.

102a, 102b, 102c denote a maximum allowable load value calculating unit for a load fracture, a maximum allowable load value calculating unit for a moment fracture, and a maximum allowable load value calculating unit for a nugget interior fracture respectively, which analyze and calculate maximum allowable load values of the welded portion in a load fracture mode, a moment fracture mode, and a nugget interior fracture mode respectively.

102d denotes an allowable load value calculating unit, which finds allowable load values at every moment after the maximum allowable load values of the welded portion calculated in the maximum allowable load value calculating units 102a to 102c are reached, to find a displacement or a time at which the allowable load values become 0.

103 denotes an output unit, which outputs detailed fracture information obtained by the maximum allowable load value calculating units 102a to 102c and the allowable load value calculating unit 102d.

Figure 2:
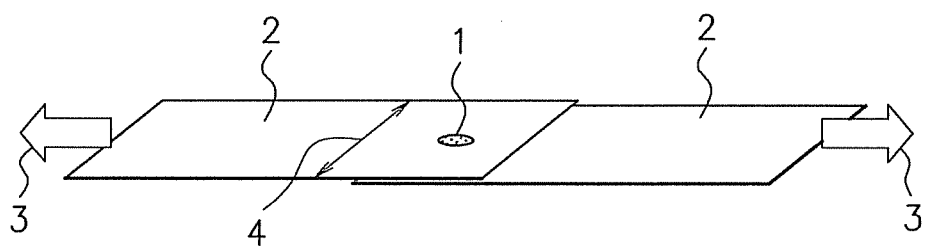
FIG. 2 is a schematic view showing an outline of a shear tensile test.

FIG. 2 is a view showing an outline of a shear tensile test. As shown in FIG. 2, in a test piece, two steel sheets being base materials 2 each having a test piece width 4 are stacked and spot-welded, whereby a nugget 1 is formed. This test piece is subjected to a tensile test until the test piece fractures in a tensile direction shown by the arrows 3. At this time, a displacement of the test piece in the tensile direction 3 and a load are measured. The fracture occurs around the nugget 1 and at this time, a strain becomes largest.

Conventional arts were applicable only to fracture modes of a load fracture which is a fracture due to a tension acting on a spot welded portion (hereinafter also referred to as a load-type base material-plug fracture) and a moment fracture which is a fracture due to a bending moment applied to an end portion of a spot welded portion (hereinafter also referred to as a moment-type base material-plug fracture), and analysis considering a plurality of fracture modes was not possible, and accordingly there have been sometimes a case where analysis results greatly differ from experimental results.

Therefore, in this embodiment, based on the sheet thickness t, the tensile strength TS, the elongation El, and the chemical composition of the nugget portion in each of the spot-welded steel sheets, the nugget diameter d of the welded portion, the effective width B determined by the distance between adjacent welded portions, edges or ridge lines, and the sectional height H, the maximum allowable load values of the welded portion in the respective fracture modes of the load fracture, the moment fracture, and the nugget interior fracture are found, and when a state amount of the spot welded portion reaches the maximum allowable load value of any of the fracture modes, it is evaluated that a fracture occurs in this fracture mode. Consequently, according to a property and a load state of the spot welded portion, it is possible to estimate a right fracture behavior even when it is not know in advance which of the fracture modes will occur. As the state amount of the spot welded portion, a load is usable for the load fracture and the nugget interior fracture, and a moment is usable for the moment fracture, but in the present application, the term, the maximum allowable load value, is used also for the moment fracture. When a finite element method is used, the welded portion is modeled by using beam element and/or solid element. As for loads and moments applied on these elements, their values are obtained as quantities each having a direction and a magnitude, and therefore they are usable in this fracture analysis method.

Figure 3:
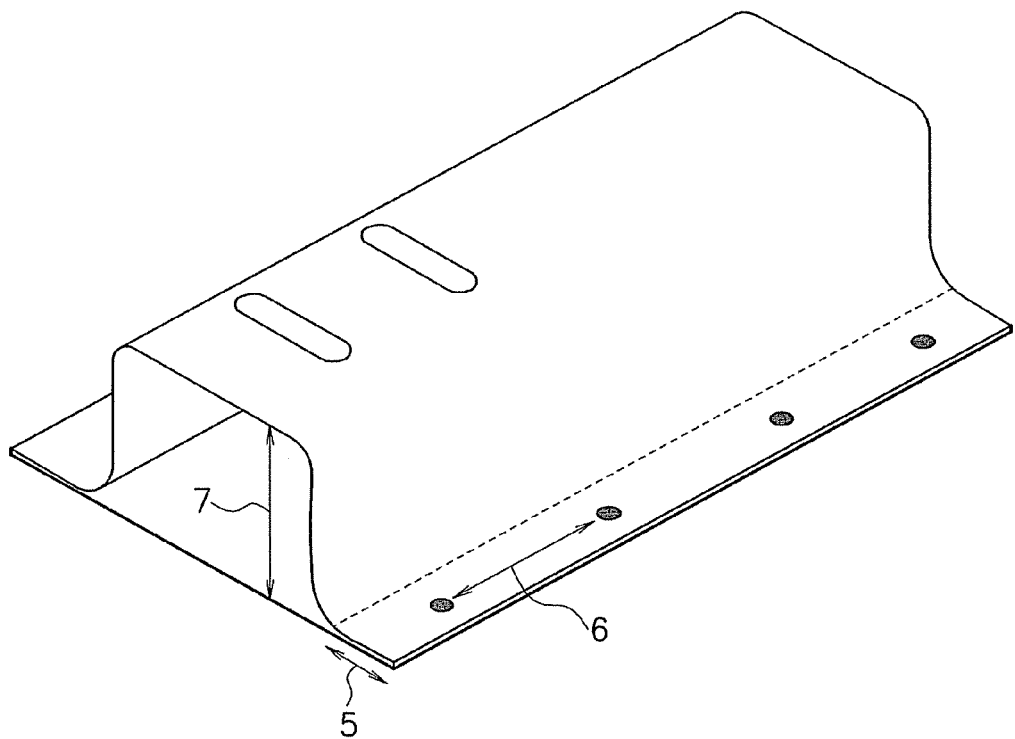
FIG. 3 is a perspective view showing an example of a member in which a plurality of spot welding points exist.

Note that the effective width B is determined by the distance between adjacent welded portions, edges or ridge lines. Concretely, in a test piece in which there is one spot welding point, it is the test piece width 4 corresponding to a distance between edges sandwiching the spot welding point as shown in FIG. 2. When there are a plurality of spot welding points, for example, in a member shown in FIG. 3, it is a distance 6 to an adjacent spot welding when a force acting on the welded portion is large in a direction perpendicular to a member longitudinal direction, and is a distance 5 between an edge and a ridge line sandwiching the welded portion when the force is large in the member longitudinal direction.

The maximum allowable load value of the moment fracture is preferably corrected by the sectional height H. Further, in finding the maximum allowable load value of the nugget interior fracture, a thickness-direction weighted average of a nugget portion carbon equivalent is preferably used. The sectional height H refers to a sectional height of a structure and refers to, for example, a height shown by the reference numeral 7 in FIG. 3.

In a method of correcting the maximum allowable load value of the moment fracture by the sectional height H, it is preferable, for example, that B' calculated by a linear function of the sectional height H as expressed by the following formula (1) is used as the effective width B determined by the distance between adjacent welded portions, edges or ridge lines, and the correction is made so that the effective width B decreases as the sectional height H becomes larger.

$$B' = B + a - b/(cH + d) \quad (1),$$

where a, b, c, d are coefficients.

Further, the maximum allowable load value of the nugget interior fracture is set as a function of the chemical composition of the nugget portion and in the welding of steel sheets different in chemical composition, an average value weighted according to the sheet thickness is used, whereby it is possible to obtain an analysis result closer to an experimental result.

Figure 4:
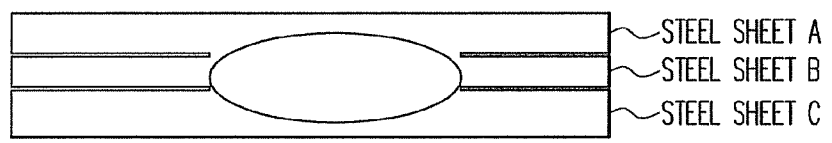
FIG. 4 is a cross-sectional view when three steel sheets A, B, C are stacked and a fracture between the steel sheets A-B is evaluated.

Further, when there are three welded steel sheets or more, two spot welded portions or more where the three steel sheets or more are joined are separately subjected to the determination, and at this time, as the sheet thickness of the steel sheet stacked on a rear surface side, a total sheet thickness of the steel sheets stacked on the rear surface side is preferably used. FIG. 4 shows an example where three steel sheets A, B, C are stacked. In spot welding, the stacked sheets are pressed by being sandwiched by electrodes and are current-heated, and at this time, the sheets melt from their center portions. When these portions are solidified again, the joining of the sheets is completed, and the elliptic portion in FIG. 4 schematically shows a nugget formed through the melting→solidification. When a fracture between the steel sheets A-B is to be evaluated, by using a total sheet thickness value of the steel sheets B and C instead of the sheet thickness of the steel sheet B side, it is possible to accurately analyze the fracture even when there are three welded steel sheets or more.

According to this embodiment, the fracture modes including the nugget interior fracture and the fracture load are known, and in addition, accuracy increases when sectional rigidity is high, when a nugget interior fracture occurs in joining steel sheets different in grade, when a fracture occurs in welded portions of three stacked sheets or more, and when a fracture occurs in a structure with multiple welding points, which facilitates taking a measure according to the fracture mode.

Further, after the maximum allowable load value of each of the fracture modes is reached, the allowable load value at every moment is found according to each of the fracture modes, and the displacement or the time at which the allowable load value becomes 0 is found. In the case of the load fracture and the moment fracture, after a minute crack occurs in base materials around the nugget, the crack passes through a periphery of the nugget and the sheet thickness of the base materials, so that a fracture occurs in the spot welded portion. Generally, since a material used for a car body has sufficient ductility, a decrease of the allowable load value due to the progress of this crack is slow. On the other hand, in the case of the nugget interior fracture, since a crack occurs in a very hard nugget (weld metal) and this propagates into the nugget relatively quickly, the allowable load value in this case quickly decreases. FIG. 5A is a chart showing a method of decreasing the allowable load value in the load fracture, FIG. 5B is a chart showing a method of decreasing the allowable load value in the moment fracture, and FIG. 5C is a chart showing a method of decreasing the allowable load value in the nugget interior fracture. The horizontal axis represents the displacement, and this represents a relative displacement between two base materials joined by spot welding. The displacement before the allowable load value becomes 0, that is, before a complete fracture occurs after the maximum allowable load value is reached can be used by referring to the sheet thickness, the nugget diameter, and so on. Incidentally, in numerical analysis, the calculation is often performed under a fixed speed condition, with a time being a control variable, and in this case, the allowable load value may be decreased by using the time instead of the displacement.

Loads acting on the spot welded portion include a force applied perpendicularly on the welded portion (nugget) (axial force), a force shearing the nugget (shear force), and bending of the nugget (moment). In the numerical analysis as well, these three kinds of force components are calculated at every moment, are compared with the maximum allowable load values, and when the maximum allowable load value is reached, it is determined that a fracture occurs. FIG. 5A to FIG. 5C show examples of how the forces applied to a welded portion change after reaching the maximum allowable load value. For example, FIG. 5A and FIG. 5C show cases where the axial force (the upper curve in the drawings) is higher than the shear force (the lower curve in the drawings), and show that the both forces are decreased after they reach the maximum allowable load value represented by the vertical line. Note that it differs from case to case which of the shear force and the axial force is higher, and FIG. 5A and FIG. 5C show only examples.

Further, by creating a program capable of executing the above-described fracture analysis method on a computer, it is possible to realize a fracture analysis computer program for a spot welded portion for causing a computer to execute: processing to find a maximum allowable load value of a welded portion in a predetermined fracture mode based on at least one of a sheet thickness t, a tensile strength TS, an elongation El, and a chemical composition of a nugget portion in each of spot-welded steel sheets, a nugget diameter d of the welded portion, an effective width B of the welded portion determined by a distance between adjacent welded portions, edges or ridge lines, and a sectional height H; and processing to find an allowable load value at every moment after the maximum allowable load value of the welded portion is reached, according to the predetermined fracture mode, to find a displacement or a time at which the allowable load value becomes 0, and by recording the program in a computer-readable storage medium, it is possible to realize versatility enabling the use by many users.

FIG. 6 is a chart showing calculation steps in this embodiment.

First, input information is read (Step S1). Input items when steel sheets A, B are spot-welded are shown in Table 1. The input items used for the determination differ depending on each fracture mode, but using all the input items listed here enables the evaluation for all the fracture modes and enables to know the fracture mode where the maximum allowable load value is reached first.

TABLE 1

| | | | load fracture mode | moment fracture mode | nugget interior fracture mode |
|---|---|---|---|---|---|
| steel sheet | steel sheet A | sheet thickness | ○ | ○ | |
| | | tensile strength | ○ | ○ | |
| | | elongation | ○ | ○ | |
| | | component | | | ○ |
| | steel sheet B | sheet thickness | ○ | ○ | |
| | | tensile strength | ○ | ○ | |
| | | elongation | ○ | ○ | |
| | | component | | | ○ |
| | welded portion shape | nugget diameter | ○ | ○ | ○ |
| | | effective width | ○ | ○ | |
| | | sectional height | | | ○ |

Next, by using the input items marked by the circles in Table 1 according to the fracture modes of the load fracture, the moment fracture, and the nugget interior fracture, the maximum allowable load values of the welded portion are calculated (Step S2).

In the present invention, a method of calculating the maximum allowable load value in each of the fracture modes is not limited, but the following method is preferably used, for instance.

First, in the case of the load fracture, a preferable method is that a shear tensile test or a cross tensile test of a test piece having a spot welded portion is conducted, a relation between a ratio d/W of the nugget diameter d (mm) to a width W (mm) of the test piece and a stress concentration factor α found by the formula (2) is found in advance, and regarding a target material having a given tensile strength, a maximum allowable load value Fs(N) of a spot welded portion in the shear tensile test is calculated by the formula (3).

$$\alpha = TS \cdot W \cdot t / F \quad (2)$$

Here,

TS: tensile strength (MPa), t: thickness (mm) of the test piece, F: fracture limit tension (N)

$$Fs = TS \cdot W \cdot t / \alpha \quad (3)$$

Further, in the case of the moment fracture, a preferable method is that a tensile test of a flange having a spot welded portion is conducted, moment efficiency γ found by the formula (4) is found in advance from a bending moment M(N·m) applied to an end portion of the spot welded portion and a full plastic moment Mp(N·m) theoretically found from a sheet thickness, a sheet width, and a strength characteristic of a test material, and a maximum allowable load value (maximum allowable moment) Mlim(N·m) of the spot welded portion in the flange tensile test is calculated by the formula (5) from the moment efficiency γ and a full plastic moment Mp' to a material having given sheet thickness, sheet width, and strength characteristic.

$$\gamma = Mp/M \quad (4)$$

$$Mlim = Mp'/\gamma \quad (5)$$

Further, in the case of the nugget interior fracture, a preferable method is that, for example, a maximum allowable load value Fs(N) of a spot welded portion is calculated by the following formula (6), by using a thickness-direction weighted average $C_{eq}$ of a nugget portion carbon equivalent expressed by the following formula (7).

$$Fs = e \times \Pi (d/2)^2 \times (f \times C_{eq} + g) \quad (6)$$

$$C_{eq} = \Sigma_{i=1}^{n} \{t_i \cdot C_{eq}^{\ i}\} / \Sigma_{i=1}^{n} \{t_i\} \quad (7)$$

Here, d: nugget diameter (mm), $C_{eq}$: thickness-direction weighted average of the nugget portion carbon equivalent, t: thickness (mm) of the test piece, i: kind of the welded test piece (i=1 to n), e, f, g: coefficient Then, at every moment, a state variable in each mode based on a load·moment output of a spot-welded element is calculated (Step S3). Note that the spot-welded element not only is one made up of one finite element in the finite element method but also is one made up of a plurality of finite elements in some case.

Next, the maximum allowable load value at Step S2 and the state variable at Step S3 are compared for each of the fracture modes (Step S4).

When the state value of any of the modes reaches the maximum allowable load value, it is thereafter determined that the fracture has occurred, the allowable load value is decreased according to subsequent relative displacements (strains) of the spot-welded element, and a displacement or a time at which the allowable load value becomes 0 is found (Step S5).

After computation of all the processes is finished, detailed fracture information is output (Step S6).

As the output of the detailed fracture information based on which it is evaluated that the fracture has occurred, not only the result to the effect that the fracture has occurred but also the fracture mode, the maximum allowable load value, and the allowable load value are output, so that the output can be used as study information regarding a cause of the fracture and improvement.

Members in an arbitrary shape joined by the spot welding are modeled by using the finite element method on the computer, and at this time, an equivalent plastic strain εp of an element joining the members, which is a model of spot welding, is sequentially calculated by the computer during the deformation in the crash analysis reproduced by the finite element method. A means for calculating this equivalent plastic strain εp relies on a general-purpose analysis code, and for example, PAM-CRASH v2002 user's manual by ESI GmbH is referred to.

By doing so, it is possible to accurately predict the fracture determination of the spot welding on the computer without any actual fabrication of members and any verification by a crash test. The use of this method makes it possible to examine, on the computer, conditions under which no fracture occurs in the spot welding, by varying the shape of the member, the material, the sheet thickness, the nugget diameter, and the welding position, which enables the design of the optimum member.

FIG. 7 is a block diagram showing an example of a computer system capable of configuring a fracture analysis device for a spot welded portion. In this drawing, 1200 denotes a computer (PC). 1201 denotes a CPU 1201, which executes device control software stored in a ROM 1202 or a hard disk (HD) 1211 or supplied from a flexible disk drive (FD) 1212 to centrally control devices connected to a system bus 1204. Each function means is configured by a program stored in the CPU 1201, the ROM 1202, or the hard disk (HD) 1211 of the PC 1200.

1203 denotes a RAM, which functions as a main memory, a work area, and so on of the CPU 1201. 1205 denotes a keyboard controller (KBC), which performs control for inputting, to a system main body, a signal input from a keyboard (B) 1209. 1206 denotes a display controller (CRTC), which controls display on a display device (CRT) 1210. 1207 denotes a disk controller (DKC), which controls accesses to the hard disk (HD) 1211 which stores a boot program (startup program: a program starting the execution (operation) of hardware and software of the personal computer), a plurality of application programs, an edit file, a user file, a network management program, and so on, and to the flexible disk (FD) 1212.

1208 denotes a network interface card (NIC), which exchanges data bi-directionally with a network printer, other network devices or other PC via a LAN 1220.

The above-described functions are realized also by the computer executing a program. Further, a means for supplying the program to the computer, for example, a computer-readable storage medium recording such a program such as CD-ROM or a transmission medium transmitting such a program such as the Internet is also applicable as an embodiment of the present invention. Further, a program product such as a computer-readable storage medium recording the aforesaid program is also applicable as an embodiment of the present invention. The aforesaid program, storage medium, transmission medium, and program product are included in the scope of the present invention. As the storage medium, usable are, for example, a flexible disk, a hard disk, an optical disk, a magneto-optic disk, CD-ROM, a magnetic tape, a nonvolatile memory, ROM, and so on.

By using such a device configuration, it is possible to realize a fracture analysis device for a spot welded portion being a fracture analysis device used in the above-described fracture analysis method for the spot welded portion, the device including: a means for finding a maximum allowable load value of a welded portion in a predetermined fracture mode based on at least one of a sheet thickness t, a tensile strength TS, an elongation El, and a chemical composition of a nugget portion in each of spot-welded steel sheets, a nugget diameter d of the welded portion, an effective width B of the welded portion determined by a distance between adjacent welded portions, edges or ridge lines, and a sectional height H; and a means for finding an allowable load value at every moment after the maximum allowable load value of the welded portion is reached, according to the predetermined fracture mode, to find a displacement or a time at which the allowable load value becomes 0.

Further, in the finite element method analysis on the computer, since it is possible to accurately predict a fracture at a portion which is modeled on the spot welding of, for example, an automobile member, it is possible to omit the verification of the fracture of the spot welded portion at the time of a crash test of an actual automobile member. Alternatively, it is possible to greatly reduce the number of times of verification tests. Further, a member design preventing the spot welding fracture based on experimental manufacture of an automobile member under varied spot welding conditions and a large-scale experiment of a crash test can be replaced by a design preventing the fracture of the spot-welded portion based on crash analysis on the computer, which can contribute to a great cost reduction and a reduction of a period of design and development.

EXAMPLE

Analysis models used in examples of the present invention are shown in Table 2. For example, an invention example 14 is an example where the maximum allowable load values in all of the load fracture mode, the moment fracture mode, and the nugget interior fracture mode are found and allowable load values at every moment after the maximum allowable load values are reached are found. In addition, the maximum allowable load value of the moment fracture is corrected by the sectional height H, and in finding the maximum allowable load value of the nugget interior fracture, the thickness-direction weighted average of the nugget portion carbon equivalent is used. Further, when the number of welded steel sheets is three or more, two spot welded portions or more where the three steel sheets or more are joined are separately subjected to the determination, and at this time, as the sheet thickness of the steel sheet stacked on the rear surface side, the total sheet thickness of the steel sheets stacked on the rear surface side is used.

On the other hand, a comparative example 1 is an example where the maximum allowable load value is found by a method different from that of the present invention without giving any consideration to the load fracture mode, the moment fracture mode, and the nugget interior fracture mode, and the allowable load value at every moment after the maximum allowable load value is reached is not found. Further, comparative examples 2, 3, 4 are examples where the maximum allowable load values are found for the load fracture mode, the moment fracture mode, and the nugget interior fracture mode respectively, but the allowable load value at every moment after the maximum allowable load value is reached is not found.

TABLE 2

| | type of fracture mode | | | other additional condition | | |
|---|---|---|---|---|---|---|
| | load fracture | moment fracture | nugget interior fracture | correction by sectional height H | use of value of average carbon equivalent | use of total sheet thickness |
| invention example 1 | ○ | X | X | X | X | X |
| invention example 2 | ○ | ○ | ○ | X | X | X |
| invention example 3 | ○ | ○ | ○ | ○ | X | X |
| invention example 4 | ○ | ○ | ○ | X | ○ | X |
| invention example 5 | ○ | ○ | ○ | X | X | ○ |
| invention example 6 | ○ | X | X | ○ | X | X |
| invention example 7 | ○ | X | X | X | X | ○ |
| invention example 8 | X | ○ | X | X | X | X |
| invention example 9 | X | ○ | X | X | ○ | X |
| invention example 10 | X | | X | X | X | ○ |
| invention example 11 | X | X | ○ | X | X | X |
| invention example 12 | X | X | ○ | X | ○ | X |
| invention example 13 | X | X | ○ | X | X | ○ |
| invention example 14 | ○ | ○ | ○ | ○ | ○ | ○ |
| comparative example 1 | X | X | X | X | X | X |
| comparative example 2 | ○ | X | X | X | X | X |
| comparative example 3 | X | ○ | X | ○ | X | X |
| comparative example 4 | X | X | ○ | X | X | X |

In invention examples 5, 7, 10, 13, 14, when three steel sheets A-B-C are stacked, a total sheet thickness of B and C was input as a sheet thickness of B for a welded portion between A-B, and a total sheet thickness of B and A was input as a sheet thickness of B for a welded portion between B-C. Note that in the following examples, tensile strength TS (MPa) is shown as the steel type and t (mm) is shown as the sheet thickness.

Example 1

An experiment condition and an experimental result of an example 1 are shown in Table 3.

TABLE 3

| | steel sheet A | | steel sheet B | | nugget diameter [mm] | width of test piece [mm] | fracture load [kN] | fracture mode |
|---|---|---|---|---|---|---|---|---|
| experiment method | steel type | sheet thickness | steel type | sheet thickness | | | | |
| tensile shear test | 590 | 1.8 | 590 | 1.8 | 6.71 | 20 | 22.8 | load fracture |

Analysis conditions and analysis results of the example 1 are shown in FIG. 8 and Table 4. In invention examples 1 to 7, the fracture mode was the load fracture and an error of the fracture load was small such as −2.6%. Since the load fracture occurs in the experiment in Table 3, the load fracture mode is preferably used for the analysis as in the invention examples 1 to 7, but in the analysis, since a force or a moment applied to a welded portion increases in accordance with the progress of the deformation, a fracture in a mode which is not the load fracture mode can be predicted. Invention examples 8 to 10 are results of the fracture determination using the moment fracture mode, and invention examples 11 to 13 are results of the fracture determination using the nugget interior fracture mode. As shown in Table 4, their accuracy of the analysis relative to the experiment is slightly worse than that of the determination using the load fracture mode, but the prediction practically accurate enough was possible. On the other hand, in the comparative example 1, an error of the fracture load was large such as 13%.

TABLE 4

| level | mode of fracture determined | fracture load (kN) | error from test result (%) |
|---|---|---|---|
| invention example 1 | load fracture | 22.2 | −2.6 |
| invention example 2 | load fracture | 22.2 | −2.6 |
| invention example 3 | load fracture | 22.2 | −2.6 |
| invention example 4 | load fracture | 22.2 | −2.6 |
| invention example 5 | load fracture | 22.2 | −2.6 |
| invention example 6 | load fracture | 22.2 | −2.6 |
| invention example 7 | load fracture | 22.2 | −2.6 |
| invention example 8 | moment fracture | 23.8 | 4.38 |
| invention example 9 | moment fracture | 23.8 | 4.38 |
| invention example 10 | moment fracture | 23.8 | 4.38 |
| invention example 11 | nugget interior fracture | 24.9 | 9.21 |
| invention example 12 | nugget interior fracture | 24.9 | 9.21 |
| invention example 13 | nugget interior fracture | 24.9 | 9.21 |
| invention example 14 | load fracture | 22.2 | −2.6 |
| comparative example 1 | — | 25.8 | 13 |

Example 2

An experiment condition an example 2 are shown in Table 5. In the invention example 1 and the comparative example 2, the fracture mode is the load fracture.

TABLE 5

| | dimension of steel sheet | | | | | welding condition | |
| | tensile strength (Mps) | sheet thickness (mm) | hat bottom portion straight line (mm) | width (mm) | sectional height (mm) | total length (mm) | spot welding interval (mm) | nugget diameter (mm) |
|---|---|---|---|---|---|---|---|---|
| type | | | | | | | | |
| member with hat-shaped section | 980 | 1.4 | 45 | 20 | 48 | 370 | 46 | 6.0 |
| test object in flat sheet shape | 980 | 1.4 | — | 100 | — | 360 | | |

In the case of the invention example 1, a fracture portion of a spot welded portion and a deformation shape of a test object well agreed with those in the experiment as shown in FIG. 9A and FIG. 9B. On the other hand, in the case of the comparative example 2, the allowable load value at every moment after the maximum allowable load value of a welded portion is reached is not found and the allowable load value is set to 0 immediately after the maximum allowable load value is reached. In this case, a chain of fractures occurred in the spot welded portions, resulting in the occurrence of fractures at all the spot welded portions of the hat-type test object, and the result did not agree with the experimental result.

Example 3

An experiment condition of an example 3 is shown in Table 6.

TABLE 6

| | hat-side steel sheet | | flat plate-side steel sheet | | nugget |
| experiment method | steel type | sheet thickness | steel type | sheet thickness | diameter [mm] |
|---|---|---|---|---|---|
| axial crushing of member with hat section | 440 | 1.6 | 590 | 1.6 | 6.32 |

Main dimensions of a test object used in the example 3 are shown below.
  hat: straight line of a hat bottom portion 45 mm, flange width 20 mm, sectional height 43 mm, total length 370 mm
  flat sheet: width 100 mm, length 360 mm
  spot welding interval: 40 mm
  Test conditions of the example 3 are shown below.
  drop weight axial crushing test: drop hammer weight 140 kg, initial speed 36 km/h
  As an effective width, a 20 mm flange width was input for a hat-side member, and 50 mm being half the width was input for the flat sheet material in all the examples, and as a result of the test, a plug fracture occurred at two welding points.
  Analysis conditions and analysis results of the example 3 are shown in FIG. 10 and Table 7. As shown in the example 1, in a test where a sectional shape is a flat sheet and rigidity is low, the experimental result is well reproduced also in the invention example 2. In the invention example 3, the fracture mode was the moment fracture. On the other hand, in the invention example 2, no fracture occurred in the analysis. In the flat sheet, no special care is necessary, but in the application to a three-dimensional shape having high sectional rigidity, the correction by the sectional height is preferably made. In the comparative example 3, the allowable load value at every moment after the maximum allowable load value of a welded portion is reached is not found, and the allowable load value is set to 0 immediately after the maximum allowable load value is reached. In this case, a chain of fractures of spot welded portions occurred, resulting in the occurrence of fractures in ten spot welded portions, and the result did not agree with the experimental result.

TABLE 7

| | input value of sectional height of hat-side member (mm) | mode of fracture determined | number of points where fracture occurs |
|---|---|---|---|
| invention example 3 | 43 | moment | 2 |
| invention example 2 | no input | no fracture determination | |
| comparative example 3 | 43 | moment | 10 |

Example 4

An experiment condition and an experimental result of an example 4 are shown in Table 8.

TABLE 8

| | steel sheet A | | steel sheet B | | nugget diameter [mm] | width of test piece [mm] | fracture load [kN] | fracture mode |
|---|---|---|---|---|---|---|---|---|
| experiment method | steel type | sheet thickness | steel type | sheet thickness | | | | |
| tensile shear test | 780 | 3.2 | 1180 | 1.2 | 4.81 | 40 | 11.1 | nugget interior fracture |

Analysis conditions and analysis results of the example 4 are shown in Table 9. As shown in the example 1, when the same materials are welded, no difference occurs therebetween. An example here is an example when different materials are joined as shown in Table 8. In the invention example 4 using a value of an average carbon equivalent of the different materials, it has been found out that the fracture mode is the nugget interior fracture, an error of the fracture load is small such as 7.2%, and good accuracy is thus obtained. In the invention example 2, instead of using the value of the average carbon equivalent, a value of a carbon equivalent of one of the materials was used in the analysis. In the invention example 2(a) where the value of the carbon equivalent of the material whose nugget interior fracture limit is lower was used in the analysis, an error of the fracture load was large such as −17%. In the invention example 2(b) where the value of the carbon equivalent of the material whose nugget interior fracture limit was higher was used in the analysis, the fracture mode was the load fracture and the result was different from the experimental result, and an error of the fracture load was large such as 31%. When the same materials are joined, no special care is necessary, but in the case of the different materials, as the carbon equivalent used in the nugget interior fracture, one obtained by weighed averaging by the sheet thickness is preferably used. Incidentally, when the same materials are joined, weighted averaging may be constantly performed since the result of the weighted averaging does not change.

TABLE 9

| | mode of fracture determined | fracture load (kN) | error from test result (%) |
|---|---|---|---|
| invention example 4 | nugget interior | 11.9 | 7.2 |
| invention example 2 (a) | nugget interior | 9.2 | −17 |
| comparative example 2 (b) | load | 14.5 | 31 |

Example 5

An experiment condition of an example 5 is shown in Table 10, and when a tensile shear test was conducted in which three steel sheets A-B-C were stacked in the order mentioned and the steel sheet A and the steel sheet C was grasped to be pulled, the steel sheet A suffered a plug fracture and the fracture load was 15.9 kN.

TABLE 10

| | steel sheet A | | steel sheet B | | steel sheet C | | nugget diameter [mm] | width of test piece [mm] |
|---|---|---|---|---|---|---|---|---|
| experiment method | steel type | sheet thickness | steel type | sheet thickness | steel type | sheet thickness | | |
| tensile shear test | 590 | 1.4 | 270 | 0.8 | 590 | 1.6 | 4.51 | 40 |

Analysis conditions and analysis results of the example 5 are shown in Table 11. In the case of the stacking of two sheets, the invention example 2 is completely the same as the invention example 5, and therefore, it is obvious that good results are exhibited also in the aforesaid examples 1 to 4. Only when an analysis target is a stack of three sheets, care is necessary. In the invention example 5, the fracture mode was the load fracture and an error of the fracture load was small. On the other hand, in the invention example 2, the fracture mode was the load fracture but an error of the fracture load was large. No special care is necessary in the case of a normal stack of two sheets, but in the case of the stack of three sheets, regarding two joint portions of interest, the total sheet thickness of another set of joined sheets is desirably used as the sheet thickness.

TABLE 11

| | mode of fracture determined | fracture load (kN) | error from test result (%) | fractured portion | fractured material |
|---|---|---|---|---|---|
| invention example 5 | load | 16.4 | 3.14 | between A-B | steel sheet A |
| invention example 2 | load | 4.3 | −72.96 | between B-C | steel sheet B |

Example 6

An experiment condition of an example 6 is shown in Table 12.

TABLE 12

| | hat-side steel sheet | | flat plate-side steel sheet | |
|---|---|---|---|---|
| experiment method | steel type | sheet thickness | steel type | sheet thickness |
| axial crushing of member with hat section | 980 | 1.4 | 980 | 1.4 |

Main dimensions of a test object used in the example 6 are shown below.
hat: straight line of a hat bottom portion 45 mm, flange width 20 mm, sectional height 48 mm, total length 370 mm
  flat sheet: width 100 mm, length 360 mm
  spot welding interval: 46 mm
  nugget diameter condition: (1) 6.0 mm, (2) 5.0 mm
  A test condition of the example 6 is shown below.
  drop weight axial crushing test: drop hammer weight 140 kg, initial speed 36 km/h
In an experimental result of the example 6, successive fractures occurred under the condition (1) and a complete fracture instantaneously occurred under the condition (2).

Analysis conditions of the example 6 are shown below. In the invention example 14, the allowable load value is gradually decreased until the elongation of a spot welded element becomes equal to the nugget diameter, for the load fracture and the moment fracture. On the other hand, for the nugget interior fracture, the allowable load value was gradually decreased until the elongation of the spot welded element became equal to the sheet thickness. In the comparative example 2, the fracture prediction in the load fracture mode was performed but when the maximum allowable load value was reached, the allowable load value was instantaneously set to 0. Up to the occurrence of the fracture, the structure is the same as that of the invention example 11. In the comparative example 4, the fracture prediction in the nugget interior fracture mode was performed, but when the maximum allowable load value was reached, the allowable load value was instantaneously set to 0. Up to the occurrence of the fracture, the structure is the same as that of the invention example 11.

In the analysis result of the example 6, under the conditions (1) and (2), the result was reproduced in the invention example 14 (the results under the condition (1) are shown in FIG. 9A and FIG. 9B). In the comparative example 2, under the condition (2), the result could be reproduced but fractures occurred in all the welding instantaneously also under the condition (1). In the comparative example 4 as well, the result could be reproduced under the condition (2) as in the comparative example 2, but fractures instantaneously occurred in all the welding also under the condition (1). It has been found out that, when the progress of welding points at which a fracture occurs needs to be evaluated in a structure having many welding points, it is important in any of the fracture modes to find the allowable load value at every moment and find the displacement or the time at which the allowable load value becomes 0, instead of instantaneously setting the allowable load value to 0 after the maximum allowable load value of the welded portion is reached. From the above-described examples, the effects of the present invention have been confirmed.

INDUSTRIAL APPLICABILITY

In the present invention, according to a predetermined fracture mode, the allowable load value at every moment after the maximum allowable load value of the welded portion is reached is found, and the displacement or the time at which the allowable load value becomes 0 is found, which makes it possible to find the allowable load value before a complete fracture occurs. Further, according to the property and the load state of the spot welded portion, it is possible to estimate a right fracture behavior even when it is not known in advance which of the fracture modes will occur. Further, the handling in the case of the three sheets or more and the output of the detailed information make it possible to facilitate consideration on the technique for the fracture prevention measure.

The invention claimed is:
1. A fracture analysis method for a spot welded portion comprising:
  finding a maximum allowable load value of a welded portion in each of the predetermined fracture mode selected from the group consisting of a load fracture, a moment fracture, and a nugget interior fracture using a formula determined in advance based on at least a sheet thickness t, a tensile strength TS, an elongation El, and a chemical composition of a nugget portion in each of spot-welded steel sheets, a nugget diameter d of the welded portion, an effective width B of the welded portion determined by a distance between adjacent welded portions, edges or ridge lines, and a sectional height H; and
  finding an allowable load value in each of the predetermined fracture mode at every moment of a plurality of moments after the maximum allowable load value of the welded portion is reached by using spot welding modeled by a finite element method according to the predetermined fracture mode, and finding a displacement or a time at which the allowable load value becomes 0.

2. The fracture analysis method for the spot welded portion according to claim 1, wherein the predetermined fracture mode is a moment fracture and the maximum allowable load value thereof is corrected by the sectional height H.

3. The fracture analysis method for the spot welded portion according to claim 1, wherein the predetermined fracture mode is a nugget interior fracture, and in finding the maximum allowable load value thereof, a thickness-direction weighted average $C_{eq}$ of a nugget portion carbon equivalent, expressed by the following formula is used as a kind i (i=1 to n) of a welded test piece:

$$C_{eq} = \Sigma_{i=1}^{n}\{t_i \cdot C_{eq}^{i}\}/\Sigma_{i=1}^{n}\{t_i\}.$$

4. The fracture analysis method for the spot welded portion according to claim 1, wherein in the step of finding the maximum allowable load value, when the number of the welded steel sheets is three or more, two welded portions or more where the three steel sheets or more are joined are separately subjected to the determination, and in the determination, as the sheet thickness of the steel sheet stacked on a rear surface side, a total sheet thickness of the steel sheets stacked on the rear surface side is adopted.

5. The fracture analysis method for the spot welded portion according to claim 1, further comprising outputting information obtained in the step of finding the maximum allowable load value and the step of finding the allowable load value.

6. A fracture analysis device for a spot welded portion comprising:
   means for finding a maximum allowable load value of a welded portion in each of the predetermined fracture mode selected from the group consisting of a load fracture, a moment fracture, and a nugget interior fracture using a formula determined in advance based on at least a sheet thickness t, a tensile strength TS, an elongation El, and a chemical composition of a nugget portion in each of spot-welded steel sheets, a nugget diameter d of the welded portion, an effective width B of the welded portion determined by a distance between adjacent welded portions, edges or ridge lines, and a sectional height H; and
   means for finding an allowable load value in each of the predetermined fracture mode at every moment of a plurality of moments after the maximum allowable load value of the welded portion is reached by using spot welding modeled by a finite element method according to the predetermined fracture mode, and finding a displacement or a time at which the allowable load value becomes 0.

7. A program causing a computer to execute:
   finding a maximum allowable load value of a welded portion in each of the predetermined fracture mode selected from the group consisting of a load fracture, a moment fracture, and a nugget interior fracture using a formula determined in advance based on at least a sheet thickness t, a tensile strength TS, an elongation El, and a chemical composition of a nugget portion in each of spot-welded steel sheets, a nugget diameter d of the welded portion, an effective width B of the welded portion determined by a distance between adjacent welded portions, edges or ridge lines, and a sectional height H; and
   finding an allowable load value in each of the predetermined fracture mode at every moment of a plurality of moments after the maximum allowable load value of the welded portion is reached by using spot welding modeled by a finite element method according to the predetermined fracture mode, and finding a displacement or a time at which the allowable load value becomes 0.

8. A non-transitory computer-readable storage medium storing a program causing a computer to execute:
   finding a maximum allowable load value of a welded portion in each of the predetermined fracture mode selected from the group consisting of a load fracture, a moment fracture, and a nugget interior fracture using a formula determined in advance based on at least a sheet thickness t, a tensile strength TS, an elongation El, and a chemical composition of a nugget portion in each of spot-welded steel sheets, a nugget diameter d of a welded portion, an effective width B of the welded portion determined by a distance between adjacent welded portions, edges or ridge lines, and a sectional height H; and
   finding an allowable load value in each of the predetermined fracture mode at every moment of a plurality of moments after the maximum allowable load value of the welded portion is reached by using spot welding modeled by a finite element method according to the predetermined fracture mode, and finding a displacement or a time at which the allowable load value becomes 0.

* * * * *

UNITED STATES PATENT AND TRADEMARK OFFICE
CERTIFICATE OF CORRECTION

| | |
|---|---|
| PATENT NO. | : 8,689,637 B2 |
| APPLICATION NO. | : 13/634365 |
| DATED | : April 8, 2014 |
| INVENTOR(S) | : Hiroshi Yoshida et al. |

It is certified that error appears in the above-identified patent and that said Letters Patent is hereby corrected as shown below:

On the Title Page, Item (54) and in the Specification, Column 1, line 1, Title, change "FRACTURE ANALYSIS METHOD, DEVICE, AND PROGRAM FOR SPOT WELDED PORTION, AND COMPUTER-READABLE RECORDING MEDIUM" to -- FRACTURE ANALYSIS METHOD, DEVICE, AND PROGRAM FOR SPOT WELDED PORTION, AND COMPUTER-READABLE STORAGE MEDIUM --;

In the Specification

Column 9, line 50, change "$C_{eq} = \Sigma_{i=1}^{n} \{t_i \cdot C_{eq}^i\} / \Sigma_{i=1}^{n} \{t_i\}$," to -- $C_{eq} = \Sigma_{i=1}^{n} \{t_i \cdot C_{eq}^i\} / \Sigma_{i=1}^{n} \{t_i\}$ --;

Column 10, line 15, change "εp" to -- εp --;

Column 10, line 19, change "εp" to -- εp --.

Signed and Sealed this
Nineteenth Day of August, 2014

Michelle K. Lee
*Deputy Director of the United States Patent and Trademark Office*